United States Patent [19]
Young et al.

[11] Patent Number: 5,741,793
[45] Date of Patent: Apr. 21, 1998

US005741793A

[54] COMPOSITIONS HAVING SYNERGISTIC FUNGITOXIC EFFECTS

[75] Inventors: David Hamilton Young, Ambler; Ronald Ross, Jr., Jamison; Richard Andrew Slawecki, Warminster, all of Pa.

[73] Assignee: Rohm and Haas Company, Philadelphia, Pa.

[21] Appl. No.: 696,284

[22] Filed: Aug. 13, 1996

Related U.S. Application Data

[60] Provisional application No. 60/002,795, Aur. 25, 1995.
[51] Int. Cl.$^6$ ............ A01N 37/00; A01N 37/02; A01N 43/58
[52] U.S. Cl. ............ 514/247; 514/248; 514/252; 514/552; 514/558
[58] Field of Search ............ 514/247, 248, 514/558, 252, 552

[56] References Cited

FOREIGN PATENT DOCUMENTS 0308404  9/1991  European Pat. Off. .

OTHER PUBLICATIONS

Jones, C.A. vol. 120 (1994) 120: 185439M.

*Primary Examiner*—Allen J. Robinson
*Attorney, Agent, or Firm*—Guy T. Donatiello

[57] ABSTRACT

Fungitoxic compositions exhibiting synergistic effects in the control of fungal growth are disclosed. The compounds are based on the combination of fatty acids and derivatives thereof with pyridazinones, and exhibit a greater than expected inhibitory effect against growth of fungi. The compounds are useful for agricultural applications including control of plant diseases, and also in control of mammalian fungal growth.

19 Claims, No Drawings

COMPOSITIONS HAVING SYNERGISTIC FUNGITOXIC EFFECTS

This is a nonprovisional application of prior pending provisional application Ser. No. 60/002,795, filed Aug. 25, 1995.

The present invention relates to compositions having synergistic effects in the control of fungi. In particular, the present invention relates to the use of fatty acids in combination with pyridazinones and related species in the control of fungal growth.

Pyridazinones are described for use in the control of fungi in European Patent Application No. EP 91-308,404.2. As used herein, "pyridazinones" includes pyridazinone compounds, dihydropyridazinones, and indenopyridazinones.

Pyridazinones are useful in controlling various fungi. Pyridazinones are particularly effective in controlling diseases of rice. Examples of rice diseases controlled by pyridazinones are seedborne diseases such as those incited by *Cochliobolus miyabeanus*, and *Pyricularia oryzae*; soil-borne rice diseases such as those incited by Fusarium species, Rhizoctonia species and Rhizopus species; and seedling box and field diseases such as those incited by *Pyricularia oryzae*, *Thanatephorus cucumeris*, and *Cochliobolus miyabeanus*. Other examples of diseases controlled by pyridazinones include cucurbit powdery mildew, incited by *Sphaerotheca fulginea*; grape powdery mildew, incited by *Uncinula necator*; and apple powdery mildew, incited by *Podosphaera leucotricha*.

It has been surprisingly discovered that, when pyridazinones are used in combination with certain fatty acids and their esters and salts, the effectiveness of the pyridazinones against fungi is unexpectedly increased over that of the pyridazinones alone.

More unexpectedly, it has been found that the particular combination of a pyridazinone with palmitic acid, pentadecanoic acid, a salt such as a sodium salt of palmitic acid or pentadecanoic acid, or an alkyl ester of said acids, provides an even higher effectiveness.

A first aspect of the present invention is a composition comprising from 99.5 percent to 10 percent of at least one fatty acid having the formula $CH_3(CHR_1)_mX(CHR_2)_nCO_2Z$, wherein $R_1$ and $R_2$ are independently selected from H, $C_1$-$C_8$ alkyl, halo and hydroxy; m and n are integers independently selected from the integers 0 through 21, such that the sum of m and n is not less than 7 and not greater than 21; X is selected from O, S, N, $CH_2$, cyclopropyl, and cyclopropenyl; Z is independently selected from the group consisting of H, alkaline metals, ammonium, alkyl ammonium, and $C_1$-$C_8$ alkyl; and from 0.5 percent to 90 percent, by weight based on total weight of the composition, of at least one pyridazinone having a formula selected from the formulas I, II, and III:

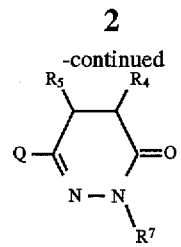

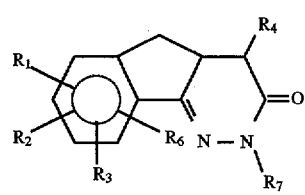

wherein Q is selected from:

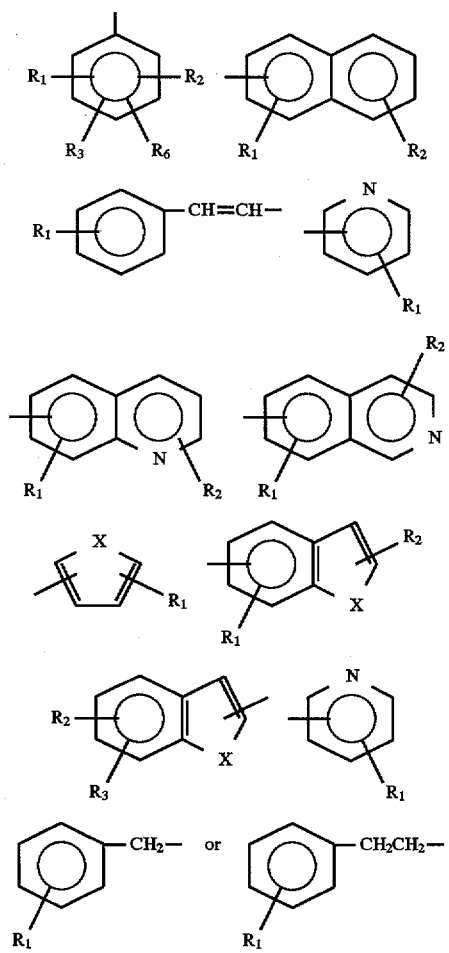

and wherein $R_3$ and $R_6$ are independently selected from hydrogen, halogen, cyano, nitro, trihalomethyl, methyl, phenyl, phenoxy, optionally substituted halo-substituted ($C_1$-$C_8$)alkyl, ($C_1$-$C_8$)alkylthio, (C1-C8) alkylsulfoxide and ($C_1$-$C_{18}$)alkoxy;

$R_4$ is selected from hydrogen, halogen, alkoxy and nitro;

$R_5$ is selected from hydrogen, halogen, nitro, alkyl, alkoxy, alkylthio, haloalkyl, haloalkoxy, haloalkylthio, phenyl, phenoxy and cyano;

$R_1$ and $R_2$ are independently selected from hydrogen, ($C_1$-$C_8$)alkyl, ($C_1$-$C_8$)alkoxy, halogen, cyano, nitro; and $R_7$ is selected from alkyl, hydroxyalkyl, cyanoalkyl, hydrazidal, heterocyclylalkyl, phenyl, phenylalkyl, phenylcarbonyl, alkenyl, haloalkenyl, phenylalkenyl, alkynylalkenyl, alkynyl, haloalkynyl, phenylalkynyl, heterocyclyl, dialkynyl, heterocyclylalkynyl, cycloalkylalkynyl, alkenylalkynyl, hydroxyalkynyl, alkoxyalkynyl, alkanoyloxyalkynyl, formylalkynyl, trialkylsilylalkynyl, trialkyltinalkynyl, haloalkenylalkynyl, carboxyalkynyl, or alkoxycarbonylalkynyl.

Another aspect of the present invention is a method for controlling phytopathogenic fungal growth on a plant by applying at the locus of the plant a fungicidally effective amount of the fungicidal composition.

One embodiment of this invention is a composition comprising from 99.5 percent to 10 percent by weight, based on the total composition, of at least one compound having the formula $CH_3(CHR_1)_mX(CHR_2)_nCO_2Z$, wherein $R_1$ and $R_2$ are independently selected front H, $C_1$–$C_8$ alkyl, halo and hydroxy; m and n are integers independently selected from the integers 0 through 21, such that the sum of m and n is not less than 7 and not greater than 21; X is selected from O, S, N, $CH_2$, cyclopropyl, and cyclopropenyl; Z is independently selected from the group consisting of H, alkaline metals, ammonium, alkyl ammonium, and $C_1$–$C_8$ alkyl; and from 0.5 percent to 90 percent, by weight based on total weight of the composition, of at least one pyridazinone having a formula selected from the formulas I, II and III, wherein $R_4$ and $R_5$ are hydrogen; Q is phenyl and is unsubstituted or substituted with from 1 to 3 substituents independently selected from halo, trihalomethyl, cyano, ($C_1$–$C_8$)alkyl, ($C_1$–$C_8$)alkylthio, ($C_1$–$C_8$)alkoxy and phenyl; and $R_7$ is selected from ($C_1$–$C_{12}$) alkyl, cyano($C_1$–$C_{12}$)alkyl, heterocyclyl($C_1$–$C_{12}$)alkyl, phenyl, phenyl($C_1$–$C_{12}$)alkyl, phenylcarbonyl, ($C_1$–$C_{12}$)alkenyl, halo($C_1$–$C_{12}$)alkenyl, phenyl($C_1$–$C_{12}$)alkenyl, alkynyl($C_1$–$C_{12}$)alkenyl, ($C_1$–$C_{12}$) alkynyl, halo($C_1$–$C_{12}$)alkynyl, cyclo($C_3$–$C_8$)alkylalkynyl, ($C_1$–$C_{12}$)alkenylalkynyl, hydroxyalkynyl, and alkoxyalkynyl.

A preferred embodiment of this invention is a composition comprising from 99.5 percent to 10 percent by weight of at least one compound having the formula $CH_3(CH_2)_nCO_2Z$, wherein n is an integer selected from the integers 12 through 18 and Z is independently selected from the group consisting of H, Na, K, ammonium and $C_1$–$C_4$ alkyl; and from 0.5 percent to 90 percent, by weight based on total weight of the composition, of at least one pyridazinone having a formula selected from the formulas I, II and III, wherein $R_4$ and $R_5$ are hydrogen; Q is phenyl and is optionally substituted with a halo moiety in at least one position selected from positions 3 and 4; and $R_7$ is selected from ($C_1$–$C_{12}$) alkyl, cyano($C_1$–$C_{12}$)alkyl, ($C_1$–$C_{12}$)alkenyl, phenyl($C_1$–$C_{12}$)alkenyl, alkynylalkenyl, ($C_1$–$C_{12}$)alkynyl, halo($C_1$–$C_{12}$)alkynyl, cyclo($C_3$–$C_8$)alkylalkynyl, ($C_1$–$C_{12}$) alkenylalkynyl, hydroxyalkynyl, and alkoxyalkynyl.

A more preferred embodiment of the present invention is a composition comprising from 99 percent to 25 percent of a compound selected from $C_{15}$–$C_{17}$ fatty acids, alkaline metal salts of $C_{15}$–$C_{17}$ fatty acids, ammonium salts of $C_{15}$–$C_{17}$ fatty acids, and $C_1$–$C_4$ esters of $C_{15}$–$C_{17}$ fatty acids; and from 1 percent to 75 percent of a pyridazinone having a formula selected from the formulas I, II and III, wherein Q is phenyl and is optionally substituted with halo at at least one position selected from positions 3 and 4; and $R_7$ is selected from ($C_1$–$C_{12}$) alkyl, cyano($C_1$–$C_{12}$)alkyl, ($C_1$–$C_{12}$)alkenyl, phenyl($C_1$–$C_{12}$)alkenyl, alkynyl($C_1$–$C_{12}$) alkenyl, ($C_1$–$C_{12}$)alkynyl, halo($C_1$–$C_{12}$)alkynyl, cyclo ($C_3$–$C_8$)alkylalkynyl, ($C_1$–$C_{12}$)alkenylalkynyl, hydroxyalkynyl, and alkoxyalkynyl.

A $C_{15}$–$C_{17}$ fatty acid will be recognized by one skilled in the art to mean a compound of the formula $CH_3(CH_2)_nCO_2Z$, wherein n is an integer selected from the integers 13 through 15 and Z is H. Unless otherwise indicated, as used herein, the term "fatty acid" also refers to the esters and salts of fatty acids within the scope of the present invention.

Most preferred is a composition comprising from 98 percent to 50 percent of a compound selected from: palmitic acid and pentadecanoic acid, alkaline metal salts of palmitic acid, organic salts of palmitic acid, ammonium salts of palmitic acid, alkaline metal salts of pentadecanoic acid, organic salts of pentadecanoic acid, ammonium salts of pentadecanoic acid, $C_1$–$C_8$ alkyl esters of palmitic acid, and $C_1$–$C_8$ alkyl esters of pentadecanoic acid; and from 2 percent to 50 percent of a pyridazinone having a formula selected from I, II and III, wherein Q is phenyl and is optionally substituted with halo at at least one position selected from positions 3 and 4; and $R_7$ is selected from ($C_1$–$C_{12}$) alkyl, cyano($C_1$–$C_{12}$)alkyl, ($C_1$–$C_{12}$)alkenyl, phenyl($C_1$–$C_{12}$)alkenyl, alkynylalkenyl, ($C_1$–$C_{12}$) alkynyl, halo($C_1$–$C_{12}$)alkynyl, cyclo($C_3$–$C_8$)alkylalkynyl, ($C_1$–$C_{12}$) alkenylalkynyl, hydroxyalkynyl, and alkoxyalkynyl.

As used herein, the term "alkyl" refers to straight carbon chains such as, for example, propyl, and to branched carbon chains such as, for example, tert-butyl. Also included are cyclic carbon compounds containing up to 7 carbon atoms, such as, for example, cyclopropyl. "Alkenyl", as in, for example, "phenylalkenyl", refers to straight carbon chains containing a double bond and having up to 8 carbon atoms. "Alkynyl", as in, for example, "haloalkynyl", refers to straight carbon chains containing a triple bond and having up to 8 carbon atoms.

The term "aryl" includes phenyl or naphthyl, which maybe substituted with up to three substituents selected from the group consisting of halogen, cyano, nitro, trihalomethyl, methyl, phenyl, phenoxy, halo-substituted ($C_1$–$C_4$)alkyl, ($C_1$–$C_4$)alkylthio, ($C_1$–$C_4$)alkylsulfoxide and ($C_1$–$C_{18}$)alkoxy.

Typical aryl substituents include but are not limited to 4-chlorophenyl, 4-fluorophenyl, 4-bromophenyl, 2-methoxyphenyl, 2,4-dibromophenyl, 3,5-difluorophenyl, 2,4,6-trichlorophenyl, 4-methoxyphenyl, 2-chloronaphthyl, 2,4-dimethoxphenyl, 4-(trifluormethyl)phenyl, 2,4-diiodonapthyl, 2-iodo-4-methylphenyl.

"Halo" is meant to include iodo, fluoro, bromo and chloro moieties.

Saturated fatty acids are known in the art for use as surfactants in agricultural chemical formulations. Saturated fatty acid compounds suitable for use in the present invention have the formula $CH_3(CH_2)_nCO_2X$, defined hereinabove, wherein n is an integer selected from 8-22. These compounds are also referred to herein as "$C_{10}$–$C_{24}$ fatty acids and derivatives", and as "fatty acids and derivatives".

Examples of salts and esters of $C_{10}$–$C_{24}$ fatty acids useful in increasing the effectiveness of a pyridazinone toward fungi are sodium salts and "short chain" alkyl esters, wherein X is selected from H, alkali metals and $C_1$–$C_8$ alkyl. As used herein, "short chain" refers to carbon chains of length $C_1$–$C_8$. The fatty acids and derivatives of the present invention may include hetero atoms such as oxygen, sulfur and nitrogen, and suitable fatty acids and derivatives may therefore include fatty acid ethers.

The pyridazinones for use in the fungicidal composition of the present invention may be prepared by conventional synthetic routes. For example, pyridazinones suitable for use in the method of the present invention were prepared according to the methods described in detail in European Patent Application no. 91-308,404.2.

Examples of pyridazinones particularly useful in the method of the present invention include 6-(4-chlorophenyl)-2-(2'-pentyn-4'-ene-1-yl)-3(2H)-pyridazinone; 6-(4-chlorophenyl)-2-(2'-pentynyl)-3(2H)-pyridazinone; 6-(4-chlorophenyl)-2-(5'-pentoxy-2'-butynyl)-3(2H)-pyridazinone; 6-(4-chlorophenyl)-2-(4'-fluoro-2'-butynyl)-3(2H)-pyridazinone; 6-(2-pyridyl)-2-(2'-nonynyl)-3(2H)-pyridazinone; 7-chloro-2,4,4a,5-tetrahydro-2-(2'-pentynyl)-indeno[1,2-c]-pyridazin-3-one; 6-(4-chlorophenyl)-2-(2'-pentynyl)-3(2H)-4,5-dihydropyridazinone; 6-(2-napthyl)-2-(2'-pentynyl)-3(2H)-pyridazinone; and 6-(4-chlorophenyl)-2-(2'-decynyl)-3(2H)-pyridazinone.

In order to obtain acceptable fungicidal activity by using the composition and method of the present invention, a fungicidally effective amount of both components of the composition must be used. As used herein, a "fungicidally effective amount" is a quantity of a compound which causes a reduction of a fungal population or decreases crop damage as compared to a control group. A fungicidally effective amount of a particular compound for use against a particular fungus will depend upon the type of equipment employed, the method and frequency of application desired, and the diseases to be controlled, but is typically from 0.01 to 20 kilograms (kg) of active compound per hectare. As a foliar fungicide, a pyridazinone is typically applied to growing plants at a rate of from 0.1 to 5, and preferably from 0.125 to 0.5 kg per hectare.

The fungicidal compositions of the present invention are useful as agricultural fungicides and, as such, can be applied to various loci such as the seed, the growth medium or the foliage. For such purposes these compounds can be used in the technical or pure form as prepared, or more typically as solutions or as formulations. The compounds are usually taken up in a carrier or are formulated so as to render them suitable for subsequent dissemination.

The fungicidal composition of the present invention may be applied according to conventional methods for the use of fungicides. The compounds to form the fungicidal composition may be applied separately, or may be combined to form the composition before applying. As discussed herein, in most applications a fungicidal composition is used with an agronomically acceptable carrier. An "agronomically acceptable carrier" is a solid or liquid which is biologically, chemically and physically compatible with the compounds of the present invention, and which may be used in agricultural applications. Agronomically acceptable carriers suitable for use in the method of the present invention include organic solvents, and finely divided solids, both exemplified herein. For example, these fungicidal compositions can be formulated as wettable powders, emulsifiable concentrates, dusts, granular formulations, aerosols, or flowable emulsion concentrates. In such formulations, the compounds are extended with a liquid or solid carrier and, when desired, suitable surfactants are incorporated.

Optional components, not required for fungicidal activity but useful or required for other properties, include, but are not limited to, adjuvants such as wetting agents, spreading agents, dispersing agents, stickers, adhesive and the like. Such adjuvants are well known in the art, and a discussion of adjuvants can be found in many references, such as in the John W. McCutcheon, Inc. publication *McCutcheon's Emulsifiers and Detergents* (published annually by McCutcheon Division of MC Publishing Company, New Jersey).

In general, the compounds of this invention may be dissolved in solvents such as acetone, methanol, ethanol, dimethylformamide, pyridine or dimethyl sulfoxide and such solutions can be diluted with water. The concentrations of the solution after dilution may vary from 1% to 90% by weight, with a preferred range being from 5% to 50%.

For the preparation of emulsifiable concentrates of the compounds of the present invention, the compound can be dissolved in suitable organic solvents, or a mixture of solvents, together with an emulsifying agent to enhance dispersion of the compound in water. The concentration of the total active ingredient in emulsifiable concentrates is usually from 10% to 90%, and in flowable emulsion concentrates, can be as high as 75%. As used herein, the term "active ingredient" refers to the total fungicidal composition, that is the combined quantity of pyridazinone and fatty acid.

Wettable powders suitable for spraying can be prepared by admixing the fungicidal composition with a finely divided solid, such as clays, inorganic silicates and carbonates, and silicas and incorporating wetting agents, sticking agents, and/or dispersing agents in such mixtures. The concentration of total active ingredients in such formulations is usually in the range of from 20% to 99% by weight, preferably from 40% to 75%. A typical wettable powder is made by blending 50 parts of a pyridazinone, 45 parts of a synthetic precipitated hydrated silicon dioxide, such as that sold under the trademark Hi-Sil®, and 5 parts of sodium lignosulfonate. To prepare a wettable powder from the compounds of the present invention, 50 parts of total active ingredients (pyridazinone and fatty acid, salt, or ester) may be used instead of 50 parts of pyridazinone. In another preparation a kaolin type (Barden) clay is used in place of the Hi-Sil in the above wettable powder, and in another such preparation 25% of the Hi-Sil is replaced with a synthetic sodium silicoaluminate sold under the trademark Zeolex®7 (J. M. Huber Corporation).

Dusts are prepared by mixing the fungicidal composition with finely divided inert solids which can be organic or inorganic in nature. Materials useful for this purpose include botanical flours, silicas, silicates, carbonates and clays. One convenient method of preparing a dust is to dilute a wettable powder with a finely divided carrier. Dust concentrates containing from 20% to 80% of the active ingredient are commonly made and are subsequently diluted to from 1% to 10% use concentration.

The fungicidal composition may be applied as fungicidal sprays by methods commonly employed, such as conventional high-gallonage hydraulic sprays, low-gallonage sprays, air-blast spray, aerial sprays and dusts. The dilution and rate of application will depend upon the type of equipment employed, the method of application, plants to be treated and diseases to be controlled. Generally, the compounds of this invention will be applied in an amount of from 0.06 to 60 kilograms (kg) per hectare and preferably from 1 to 28 kg per hectare of the active ingredient.

As a seed protectant, the fungicidal composition may be coated on the seed. The usual dosage rate is from 0.05 ounce of "active ingredient" per hundred pounds of seed, to 20 ounces per hundred pounds of seed, preferably from 0.05 to 4 ounces per hundred pounds of seed, and more preferably from 0.1 to 1 ounce per hundred pounds of seed. As a soil fungicide the fungicidal composition may be incorporated in the soil or applied to the surface usually at a rate of from 0.02 to 20, preferably from 0.05 to 10, and more preferably from 0.1 to 5 kg per hectare. As a foliar fungicide, the fungicidal composition may be applied to growing plants at a rate of from 0.01 to 10 kg per hectare, preferably from 0.02 to 6 kg per hectare, and more preferably from 0.3 to 1.5 kg per hectare.

The fungicidal compounds of the present invention may be combined with other known fungicides to provide broad spectrum activity. Suitable fungicides for use in combination with the fungicidal compounds of the present invention include, but are not limited to, those compounds listed in U.S. Pat. No. 5,252,594 (see in particular columns 14 and 15).

The fungicidal compositions of the present invention also have biocidal applications as, for example, wood preservatives and marine anti-foulants. Accordingly, the present invention also encompasses the use of the disclosed compositions as wood preservatives and marine antifoulants.

Another application for these fungicidal compositions is as mammalian antimycotic agents, including use as human antimycotic agents. The present invention therefore also encompasses the use of the disclosed compositions as mammalian antimycotic agents. When used as mammalian antimycotic agents, the compositions of the present invention must include pharmaceutically acceptable carriers. The term "pharmaceutically acceptable carriers" is meant to include any solvents, dispersion media, coatings, and adsorption delaying agents. The use of pharmaceutically acceptable carriers is well known in the art. The type of pharmaceutically acceptable carrier used will depend upon the method of administration of the agent and dosage required. The method and dosage are expected to be determined according to standard procedures for the administration of anti-mycotic agents.

The following examples are intended to illustrate the fungicidal compositions of the present invention and their effectiveness.

EXAMPLE 1

Effects of Fatty Acids and Esters on Fungitoxicity of 6-(4-chlorophenyl)-2-(2'-pentynyl)-3(2H)-pyridazinone Towards *Saccharomyces cerevisiae*

Fifty milliliters (ml) of YPG culture medium (10 grams (g) yeast extract, 20 g peptone, and 20 g glucose per liter of water) in a 250 ml Erlenmeyer flask was inoculated with *Saccharomyces cerevisiae* (strain X2180-1A) to give an Absorbance at 700 nanometers (nm) of 0.02. This culture was incubated for 18 hours at 30° C. with shaking at 225 rpm. The cells were harvested by centrifugation, washed once with SD medium (6.7 g Bacto-yeast nitrogen base (Difco Laboratories, Detroit, Mich.)) and 20 g glucose per liter of water), and suspended in SD medium to give an Absorbance at 700 nm of 0.04. Aliquots (5 ml) of cell suspension were distributed in 20 ml capacity glass vials. Treatments containing 6-(4-chlorophenyl)-2-(2'-pentynyl)-3(2H)-pyridazinone ("PD2") received 25 microliters (µl) of a 100 microgram (µg)/ml solution of PD2 in dimethylsulfoxide (DMSO) providing a concentration of 0.5 parts per million (ppm). Treatments without PD2 received 25 µl DMSO. Treatments containing fatty acids received 25 µl of a 2 mM solution of fatty acid in a 1% solution of Triton X-100 providing a concentration of 10 micromolar (µM). Treatments without fatty acid received 25 µl of 1% Triton X-100. All treatments were carried out in duplicate. Vials were incubated for 22 h at 30° C. with shaking at 225 rpm. Growth of the cells was then estimated by diluting the cells in each treatment 3-fold with SD medium and measuring the Asorbance at 700 nm. Inhibition of growth was determined by comparing growth in the treatment with PD2 with growth in controls without either PD2 or fatty acid. Degree of inhibition is expressed as a percentage in Table 1.

Expected inhibition of growth was calculated using the Colby formula, which is known to those skilled in the art (R. S. Colby, *Weeds* 15, 20–22 (1967). The Colby formula, as used herein to calculate the expected inhibition of fungal growth by the combination of a fatty acid and a pyridazinone commpound, is:

$$E = x + y - [(x \cdot y)/100]$$

where: E is the expected inhibition of fungal growth, expressed as a percentage of growth in a control sample with no pyridazinone or fatty acid; x is the inhibition of growth produced by the pyridazinone compound alone, expressed as a percentage of growth in a control sample with no pyridazinone or fatty acid; and y is the inhibition of fungal growth produced by the fatty acid alone, expressed as a percentage of growth in a control sample with no pyridazinone or fatty acid. This formula was used to determine the expected inhibition of fungal growth in all examples.

TABLE 1

Effects of fatty acids and esters on fungitoxicity of 6-(4-chlorophenyl)-2-(2'-pentynyl)-3(2H)-pyridazinone towards *Saccharomyces cerevisiae*

| Fatty acid | Observed inhibition (%) without PD 2* | Observed inhibition (%) with PD 2 | Expected inhibition (%) |
|---|---|---|---|
| None | 0 | 14.6 | |
| Pentadecanoic (15:0) | 0.14 | 65.2 | 14.7 |
| Palmitic (16:0) | −1.4 | 83.0 | 13.3 |
| Heptadecanoic (17:0) | 5.5 | 54.3 | 19.2 |
| Methyl pentadecanoate | 9.3 | 72.8 | 22.5 |
| Methyl palmitate | 8.8 | 49.0 | 22.0 |
| Ethyl palmitate | 10.5 | 32.2 | 23.5 |
| Propyl palmitate | 9.9 | 29.3 | 23.0 |
| Isopropyl palmitate | 6.6 | 25.7 | 20.2 |
| Na palmitate | −1.1 | 83.6 | 13.6 |
| Hexadecamide | 12.2 | 32.3 | 25.0 |

*PD 2: 6-(4-chlorophenyl)-2-(2'-pentynyl)-3(2H)-pyridazinone

The results in Table 1 demonstrate that growth is more inhibited by PD2 in combination with fatty acids or esters than expected based on the inhibition by each component when used alone (using the Colby formula). The increase in inhibition of growth ranges from about 27% (for example, propyl palmitate and isopropyl palmitate) to about 500% (for example, palmitic acid).

EXAMPLE 2

Effect of Palmitic Acid on Fungitoxicity of PDs Towards *Saccharomyces cerevisiae*

Pyridazinones were dissolved in DMSO at 4 mg/ml, then diluted 20-fold into SD medium with and without 50 micromolar (µM) palmitic acid. Two-fold serial dilutions of the resulting 200 ppm solutions (100 microliter (µl)) were prepared in wells of 96-well microtiter plates in SD medium with and without 50 µM palmitic acid. Each well was inoculated with 100 µl of a suspension of *Saccharomyces cerevisiae* cells (strain X2180-1A) at a density of $10^4$ cells/ml in SD medium (cell suspension prepared as in Example 1). After inoculation, microtiter plates were incubated at 30° C. for 48 h after which minimum inhibitory concentration (MIC) values were determined by visual inspection. All assays were conducted in duplicate. Where MIC values from the duplicate tests differed, both values are given. MIC values for different pyridazinones in the presence and absence of palmitic acid are shown in Table 2.

TABLE 2

Effect of palmitic acid on fungitoxicity of PDs towards *Saccharomyces cerevisiae*

| Compound | Without palmitic acid MIC (ppm) | With palmitic acid MIC (ppm) |
|---|---|---|
| None | >50 | >50 |
| PD 1 | 1.56, 3.12 | 0.20, 0.39 |
| PD 2 | 3.12, 6.25 | 0.10, 0.20 |
| PD 3 | 3.12, 6.25 | 0.78, 1.56 |
| PD 4 | 12.5 | 3.12 |
| PD 5 | 12.5, 25 | 3.12, 6.25 |
| PD 6 | >50 | 3.12, 6.25 |
| PD 7 | >50 | 6.25 |
| PD 8 | >50 | 25 |
| PD 9 | >50 | 50 |

The data in Table 2 indicate that palmitic acid lowers the MIC for all PDs. The MIC may be drastically reduced by at least a factor of 4 (for example, PD5). Key to pyridazinone compounds in Table 2

PD 1 6-(4-chlorophenyl)-2-(2'-pentyn-4'-ene-1-yl)-3(2H)-pyridazinone
PD 2 6-(4-chlorophenyl)-2-(2'-pentynyl)-3(2H)-pyridazinone
PD 3 6-(4-chlorophenyl)-2-(5'-pentoxy-2'-butynyl)-3(2H)-pyridazinone
PD 4 6-(4-chlorophenyl)-2-(4'-fluoro-2'-butynyl)-3(2H)-pyridazinone
PD 5 6-(2-pyridyl)-2-(2'-nonynyl)-3(2H)-pyridazinone
PD 6 7-chloro-2,4,4a,5-tetrahydro-2-(2'-pentynyl)-indeno[1,2-c]-pyridazin-3-one
PD 7 6-(4-chlorophenyl)-2-(2'-pentynyl)-3(2H)-4,5-dihydropyridazinone
PD 8 6-(2-naphthyl)-2-(2'-pentynyl)-3(2H)-pyridazinone
PD 9 6-(4-chlorophenyl)-2-(2'-decynyl)-3(2H)-pyridazinone

EXAMPLE 3

Effect of Saturated Fatty Acids on Fungitoxicity of 6-(4-Chlorophenyl)-2-(2'-Pentynyl)-3(2H)-Pyridazinone Toward *Pyricularia oryzae*

Stock cultures of *Pyricularia oryzae*, causal agent of rice blast disease, were grown on potato dextrose agar. Three plugs, 9 mm diameter, cut from the growing edge of such cultures were transferred to 100 ml of YEG culture medium (4 g yeast extract and 20 g glucose per liter of water) in a 250 ml Erlenmeyer flask. This culture was incubated for 48 h at 30° C. with shaking at 200 rpm. The mycelial growth was harvested by centrifugation, resuspended in 500 ml YEG medium, and homogenized in a blender. Aliquots (5 ml) of cell suspension were distributed in 20 ml capacity glass vials. Treatments containing 6-(4-chlorophenyl)-2-(2'-pentynyl)-3(2H)-pyridazinone (PD2) received 25 µl of a 3 ppm solution in dimethylsulfoxide (DMSO) providing a concentration of 0.015 ppm. Controls without PD2 received 25 µl DMSO. Treatments containing fatty acids received 25 µl of a stock solution of fatty acid in DMSO, and controls without fatty acid received 25 µl of DMSO. All assays were carried out in triplicate. Vials were incubated for 48 h at 30° C. with shaking at 200 rpm, after which the increase in mycelial dry weight was determined. Inhibition of growth was determined by comparing growth in the treatment with PD2 with growth in controls without either PD2 or fatty acid. Degree of inhibition is expressed as a percentage in Table 3.

TABLE 3

| | Fatty acid | Concn. (µM) | Control % inhibition | + PD 2 % inhibition | **Expected % inhibition |
|---|---|---|---|---|---|
| Experiment 1: | None | | 0 | 40.1 | |
| | Palmitic (16:0)[1] | 10 | 0 | 78.4 | 40.1 |
| | Pentadecanoic (15:0) | 10 | 0 | 84.2 | 40.1 |
| Experiment 2: | None | | 0 | 30.8 | |
| | Palmitic (16:0) | 10 | 0 | 60.4 | 30.8 |
| | Heptadecanoic (17:0) | 10 | 0 | 58.7 | 30.8 |
| Experiment 3: | None | | 0 | 69.1 | |
| | Palmitic (16:0) | 10 | 0 | 93.6 | 69.1 |
| | Tridecanoic (13:0) | 10 | 33.5 | 89.8 | 79.5 |
| | Myristic (14:0) | 5 | 13.8 | 75.8 | 73.4 |

The results indicate that palmitic acid increased the inhibitory effect of PD2 by from about 35 percent to about 95 percent. Pentadecanoic acid increased the effectiveness of PD2 by more than 90 percent, and heptadecanoic acid increased the effectiveness of PD2 by about 90 percent. Tridecanoic acid increased the effectiveness of PD2 by about 10 percent and myristic acid increased the effectiveness of PD2 by about 3 percent.

What is claimed is:

1. A fungicidal composition comprising synergistic fungicidally effective amounts of:

(1) at least one fatty acid having the formula $CH_3(CH_2)_nCO_2Z$, wherein n is an integer selected from the integers 11 through 17,; Z is independently selected from the group consisting of: H, alkaline metals, ammonium, $(C_1-C_3)$ alkyl ammonium and $(C_1-C_3)$ alkyl; and (2) at least one pyridazinone having a formula selected from the formulas I, II, and III:

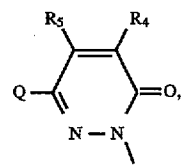

I

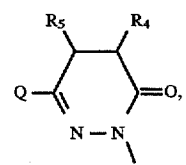

II and

-continued

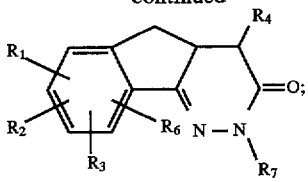

III wherein Q is selected from:

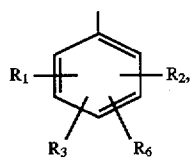

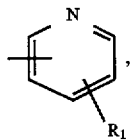

and

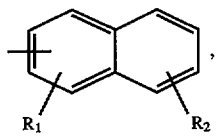

and wherein:

$R_1, R_2, R_3, R_4, R_5,$ and $R_6$ are each independently selected from the group consisting of hydrogen and halogen; and $R_7$ is selected from alkynylalkenyl, alkynyl, haloalkynyl, alkenylalkynyl, and alkoxyalkynyl.

2. The composition of claim 1 wherein n is an integer selected from the integers 13 through 17 and Z is independently selected from the group consisting of H, Na, K, ammonium and $C_1$–$C_3$ alkyl.

3. The composition of claim 1 wherein n is an integer selected from the integers 13 through 15 and Z is independently selected from the group consisting of H, Na, K, ammonium and $C_1$–$C_3$ alkyl.

4. The composition of claim 1 wherein the fatty acid is selected from the group consisting of: palmitic acid; ($C_1$–$C_3$) alkyl esters of palmitic acid; potassium salts of palmitic acid; sodium salts of palmitic acid; ammonium salts of palmitic add; pentadecanoic acid; ($C_1$–$C_3$) alkyl esters of pentadecanoic acid; potassium salts of pentadecanoic acid; sodium salts of pentadecanoic acid; ammonium salts of pentadecanoic acid; heptadecanoic acid ($C_1$–$C_3$) alkyl esters of heptadecanoic acid; potassium salts of heptadecanoic acid; sodium salts of heptadecanoic acid; and ammonium salts of heptadecanoic acid.

5. The composition of claim 1 wherein at least one pyridazinone is selected from: 6-(4-chlorophenyl)-2-(2'-pentyn-4'-ene-1-yl)-3(2H)-pyridazinone; 6-(4-chlorophenyl)-2-(2'-pentynyl)-3(2H)-pyridazinone; 6-(4-chlorophenyl)-2-(5'-pentoxy-2'-butynyl)-3(2H)-pyridazinone; 6-(4-chlorophenyl)-2-(4'-fluoro -2'-butynyl)-3 (2H)-pyridazinone; 6-(2-pyridyl)-2-(2'-nonynyl)-3(2H)-pyridazinone; 7-chloro-2,4,4a,5-tetrahydro-2-(2'-pentynyl)-indeno[1,2-c]-pyridazin-3-one; 6-(4-chlorophenyl)-2-(2'-pentynyl)-3(2H)-4,5-dihydropyridazinone; 6-(2-naphthyl)-2-(2'-pentynyl)-3(2H)-pyridazinone; and 6-(4-chlorophenyl)-2-(2'-decynyl)-3(2H)-pyridazinone.

6. The composition of claim 1 wherein the at least one pyridazinone is selected from: 6-(4-chlorophenyl)-2-(2'-pentyn-4'-ene-1-yl)-3(2H)-pyridazinone; 6-(4-chlorophenyl)-2-(2'-pentynyl)-3(2H)-pyridazinone; 6-(4-chlorophenyl)-2-(5'-pentoxy-2'-butynyl)-3(2H)-pyridazinone; 6-(4-chlorophenyl)-2(4'-fluoro-2'-butynyl)-3 (2H)-pyridazinone; 6-(2-pyridyl)-2-(2'-nonynyl)-3(2H)-pyridazinone; 7-chloro-2,4,4a,5-tetrahydro-2-(2'-pentynyl)-indeno[1,2-c]-pyridazin-3-one; 6-(4-chlorophenyl)-2-(2'-pentynyl)-3(2H)-4,5-dihydropyridazinone; 6-(2-naphthyl)-2-(2'-pentynyl)-3(2H)-pyridazinone; and 6-(4-chlorophenyl)-2-(2'-decynyl)-3(2H)-pyridazinone; and the fatty acid is selected from the group consisting of: palmitic acid; ($C_1$–$C_3$) alkyl esters of palmitic acid; potassium salts of palmitic acid; sodium salts of palmitic acid; ammonium salts of palmitic acid; pentadecanoic acid; ($C_1$–$C_3$) alkyl esters of pentadecanoic acid; potassium salts of pentadecanoic acid; sodium salts of pentadecanoic acid; ammonium salts of pentadecanoic acid; heptadecanoic acid; ($C_1$–$C_3$) alkyl esters of heptadecanoic acid; potassium salts of heptadecanoic acid; sodium salts of heptadecanoic acid; and ammonium salts of heptadecanoic acid.

7. A composition for controlling phytopathogenic fungi, comprising an agronomically acceptable carrier and a synergistic fungicidally effective amount of the composition of claim 1.

8. A composition having mammalian antimycotic activity, comprising a pharmaceutically acceptable carrier and a synergistic antimycotically effective amount of the composition of claim 1.

9. The composition of claim 1, wherein n is 14 and Z is independently selected from the group consisting of H, Na, K, ammonium and $C_1$–$C_3$ alkyl.

10. The composition of claim 1, wherein the fatty acid has the formula: $CH_3(CH_2)_nCO_2Z$, wherein n is 14 and Z is independently selected from the group consisting of H, Na, K, ammonium and $C_1$–$C_3$ alkyl; and at least one pyridazinone is selected from: 6-(4-chlorophenyl)-2-(2'-pentyn-4'-ene-1-yl)-3(2H)-pyridazinone; 6-(4-chlorophenyl)-2-(2'-pentynyl)-3(2H)-pyridazinone; 6-(4-chlorophenyl)-2-(5'-pentoxy-2'-butynyl)-3(2H)-pyridazinone; 6-(4-chlorophenyl)-2-(4'-fluoro-2'-butynyl)-3(2H)-pyridazinone; 6-(2-pyridyl)-2-(2'-nonynyl)-3(2H)-pyridazinone; 7-chloro-2,4,4a,5-tetrahydro-2-(2'-pentynyl)-indeno[1,2-c]-pyridazin-3-one; 6-(4-chlorophenyl)-2-(2'-pentynyl)-3(2H)-4,5-dihydropyridazinone; 6-(2-naphthyl)-2-(2'-pentynyl)-3 (2H)-pyridazinone; and 6-(4-chlorophenyl)-2-(2'-decynyl)-3(2H)-pyridazinone.

11. The composition of claim 1, wherein n is 14 and Z is independently selected from the group consisting of H, Na, K, ammonium and $C_1$–$C_3$ alkyl; and wherein Q is selected from:

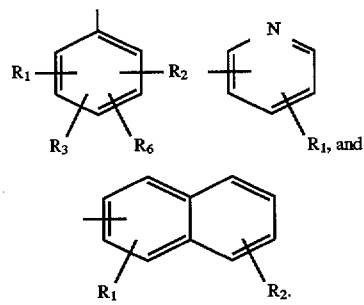

12. The composition of claim 1, wherein the fatty acid has the formula: $CH_3(CH_2)_nCO_2Z$, wherein n is 14 and Z is independently selected from the group consisting of H, Na, K, ammonium and $C_1$–$C_4$ alkyl; and wherein Q is

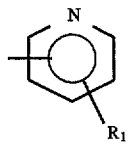

13. The composition of claim 1, wherein the fatty acid has the formula: $CH_3(CH_2)_nCO_2Z$, wherein n is 14 and Z is independently selected from the group consisting of H, Na, K, ammonium and $C_1$–$C_4$ alkyl; and wherein Q is

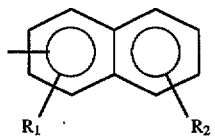

14. The composition of claim 1, wherein the fatty acid is palmitic acid and the pyridazinone is 6-(4-chlorophenyl)-2-(2'-pentynyl)-3(2H)-pyridazinone.

15. A method for controlling phytopathogenic fungal growth on a plant, comprising applying at the locus of the plant a synergistic fungicidally effective amount of the composition of claim 1.

16. A method for controlling phytopathogenic fungal growth on a plant, using a synergistic fungicidally effective amount of the composition of claim 1, comprising applying at the locus of the plant the composition of claim 1 at a rate of from 0.06 kilograms per hectare to 56 kilograms per hectare.

17. A method for controlling a fungal infection of a mammal comprising administering to said mammal a composition comprising a pharmaceutically acceptable carrier and a synergistic fungicidally effective amount of the composition of claim 1.

18. A method for controlling fungi on wood comprising treating the wood with a synergistic fungicidally effective amount of the composition of claim 1.

19. A method for controlling fungi on a surface in a marine environment, comprising treating the surface with a synergistic fungicidally effective amount of the composition of claim 1.

* * * * *